US009506114B2

(12) United States Patent
Thomson et al.

(10) Patent No.: US 9,506,114 B2
(45) Date of Patent: Nov. 29, 2016

(54) IDENTIFYING GENETIC VARIATION IN AFFECTED TISSUES

(75) Inventors: James Thomson, Madison, WI (US); Nicholas Seay, Charlottesville, VA (US)

(73) Assignee: Cellular Dynamics International, Inc., Madison, WI (US)

( * ) Notice: Subject to any disclaimer, the term of this patent is extended or adjusted under 35 U.S.C. 154(b) by 785 days.

(21) Appl. No.: 13/392,776

(22) PCT Filed: Aug. 26, 2010

(86) PCT No.: PCT/US2010/046735
§ 371 (c)(1),
(2), (4) Date: Jul. 27, 2012

(87) PCT Pub. No.: WO2011/025852
PCT Pub. Date: Mar. 3, 2011

(65) Prior Publication Data
US 2012/0322670 A1    Dec. 20, 2012

Related U.S. Application Data

(60) Provisional application No. 61/237,908, filed on Aug. 28, 2009.

(51) Int. Cl.
*C12Q 1/68* (2006.01)
(52) U.S. Cl.
CPC ....... *C12Q 1/6881* (2013.01); *C12Q 2600/154* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,863,849 A * | 9/1989 | Melamede | C12Q 1/6858 435/6.16 |
| 5,800,992 A * | 9/1998 | Fodor | B01J 19/0046 435/6.12 |
| 6,117,675 A | 9/2000 | Van der Kooy et al. | |
| 7,195,870 B2 | 3/2007 | Olek et al. | |
| 7,238,323 B2 * | 7/2007 | Knapp | B01L 3/0262 422/68.1 |
| 2006/0046258 A1 * | 3/2006 | Lapidus | C12Q 1/6869 435/6.12 |
| 2010/0167286 A1 * | 7/2010 | Reijo Pera | C12Q 1/6883 435/6.16 |
| 2011/0274662 A1 * | 11/2011 | Malcuit et al. | 424/93.7 |

FOREIGN PATENT DOCUMENTS

WO    WO 2009/061442    5/2009

OTHER PUBLICATIONS

Lee et al., "Modelling pathogenesis and treatment of familial dysautonomia using patient-specific iPSCs" Nature, vol. 461, p. 402-408 (published online Aug. 19, 2009).*
Slaugenhaupt et al., "Tissue-Specific Expression of a Splicing Mutation in the IKBKAP Gene Causes Familial Dysautonomia", American Journal of Human Genetics, vol. 68, p. 598-605 (2001).*
Meyer et al., "Modeling early retinal development with human embryonic and induced pluripotent stem cells", PNAS, vol. 106, No. 39, p. 16698-16703, (published online Aug. 25, 2009).*
Soldner et al., "Parkinson's Disease Patient-Derived Induced Pluripotent Stem Cells Free of Viral Reprogramming Factors", Cell, Vo. 136, p. 964-977, (Mar. 6, 2009).*
Maherali et al., "Directly Reprogrammed Fibroblasts Show Global Epigenetic Remodeling and Widespread Tissue Contribution", Cell Stem Cell, vol. 1, p. 55-70, (2007).*
Park et al., "Disease-Specific Induced Pluripotent Stem Cells", Cell, vol. 134, p. 877-886 (2008).*
Chim et al., "Systematic Search for Placental DNA-Methylation Markers on Chromosome 21: Toward a Maternal Plasma-Based Epigenetic Test for Fetal Trisomy 21", Clinical Chemistry, 54:3, p. 500-511 (2008).*
Judson et al., "Embryonic stem cell-specific microRNAs promote induced pluripotency", Nature Biotechnology, vol. 27, No. 5, p. 459-461 (May 2009).*
Wilson et al., "MicroRNA Profiling of Human-Induced Pluripotent Stem Cells", Stem Cells and Development, vol. 18, No. 5, p. 749-757 (2009).*
Dimos et al., "Induced Pluripotent Stem Cells Generated from Patients with ALS Can Be Differentiated into Motor Neurons", Science, vol. 321, p. 1218-1221 (2008).*
Hanna et al. Treatment of sickle cell anemia mouse model with iPS cells generated from autologous skin. Science, vol. 318, pp. 1920-1923, 2007.*
Radeke et al. Disease susceptibility of the human macula: Differential gene transcription in ther etinal pigmented epithelium/choroid. Experimental Eye Research, vol. 85, pp. 366-380, Jun. 2007.*
Gilchrist, "Medical genetics: 3. An approach to the adult with a genetic disorder," CMAJ, 167(9):1021-1029, 2002.
Gingeras et al., "Fifty years of molecular (DNA/RNA) diagnostics," *Clinical Chemistry*, 51(3):661-671, 2005.
Hirami et al., "Generation of retinal cells from mouse and human induced pluripotent stem cells," *Neuroscience Letters*, 458:126-131, 2009.
Johnson et al., "Polymorphisms affecting gene regulation and mRNA processing: Broad implications for pharmacogenetics," *Pharmacology & Therapeutics*, 106:19-38, 2005.
Kennan et al., "Identification of an *IMPDH1* mutation in autosomal dominant retinitis pigmentosa (RP10) revealed following comparative microarray analysis of transcripts derived from retinas of wild-type and Rho-/- mice," *Human Molecular Genetics*, 11(5):547-558, 2002.

(Continued)

*Primary Examiner* — Jennifer Dunston
(74) *Attorney, Agent, or Firm* — Parker Highlander PLLC

(57) ABSTRACT

Methods for the determination of tissue-specific genetic variation are provided. For example, in certain aspects methods for using iPS cell-derived specific cell types for differential molecular analysis of tissue-specific genetic variation are described.

10 Claims, No Drawings

(56) References Cited

OTHER PUBLICATIONS

Kwan et al., "Tissue effect on genetic control of transcript isoform variation," *PLoS Genetics*, 5(8):e1000608, 2009.

Lage et al., "A lage-scale analysis of tissue specific pathology and gene expression of human disease genes and complexes," *PNAS*, 105(52):20870-20875, 2008.

Lee et al., "Modelling pathogenesis and treatment of familial dysautonomia using patient-specific iPSCs," *Nature*, 461(7262):402-407, 2009.

Li et al., "Rapid and sensitive detection of messenger RNA expression for molecular differential diagnosis of renal cell carcinoma," *Clinical Cancer Research*, 9:6441-6446, 2003.

MacLaren et al., "Retinal repair by transplantation of photoreceptor precursors," *Nature*, 444:203-207, 2006.

Meyer et al., "Modeling early retinal development with human embryonic and induced pluripotent stem cells," *Proceedings of the National Academy of Sciences of the United States*, 106(39):16698-16703, 2009.

Nishikawa et al., "The promise of human induced pluripotent stem cells for research and therapy," *Nature Reviews Molecular Cell Biology*, 9(9):725-729, 2008.

Osakada et al., "In vitro differentiation of retinal cells from small-molecule induction," *Journal of Cell Science*, 122(17):3169-3179, 2009.

Oskada et al., "Toward the generation of rod and cone photoreceptors from mouse, monkey and human embryonic stem cells," *Nature Biotechnology*, 26(2):215-224, 2008.

Park et al., "Disease-specific induced pluripotent stem cells," *Cell*, 134(5):877-886, 2008.

PCT International Search Report and Written Opinion issued in International application No. PCT/US2010/046735, dated Nov. 15, 2010.

Stranger et al., "Population genomics of human gene expression," *Nat. Genet.*, 39(10):1217-1224, 2007.

Ji et al., "Elevated coding mutation rate during the reprogramming of human somatic cells into induced pluripotent stem cells," *Stem Cells*, 30:435-440, 2012.

Office Action issued in Japanese Application No. 2012-526962, mailed Nov. 19, 2014, and English language translation thereof.

Sugiura et al., "Induced pluripotent stem cell generation-associated point mutations arise during the initial stages of the conversion of these cells," *Stem Cell Reports*, 2:52-63, 2014.

\* cited by examiner

IDENTIFYING GENETIC VARIATION IN AFFECTED TISSUES

The present application is a national phase application under 35 U.S.C. §371 of International Patent Application No. PCT/US2010/046735 filed Aug. 26, 2010, which claims benefit of priority to U.S. Provisional Application Ser. No. 61/237,908 filed on Aug. 28, 2009, the entire contents of which are hereby incorporated by reference.

BACKGROUND OF THE INVENTION

1. Field of the Invention

The present invention relates generally to the field of molecular diagnosis. More particularly, it concerns the use of induced pluripotent stem cells (iPS cells) in determination and characterization of genetic variation.

2. Description of Related Art

Pathology caused by defects in human genes is usually highly tissue-specific. In heritable diseases, this suggests that specific spatiotemporal functions of the implicated genes are disrupted due to germ-line mutations. Although it has been shown that disease genes generally tend to be expressed in a limited number of tissues, it is still unclear in many cases how the tissue-specific expression patterns or genetic structure of disease genes correlate with their pathological or abnormal manifestations, and it remains difficult to determine or characterize the abnormal genes or genetic structure in certain tissue or cell types.

In a broader aspect, understanding genetic variation is a key goal of human genetics, encompassing disease susceptibility, variable response to drugs and ultimately treatment and public health.

The human body is assembled from more than 200 cell types present in a variety of tissue types. For identifying unknown genetic defects or determining genetic variation, specific cell types need to be isolated and characterized. However, some cell types may be hard to obtain from a human subject in vivo, such as the highly specialized retinal pigment epithelium (RPE) cells. Thus, there remains a need to develop more convenient methods to provide specific cell types to analyze the tissue-specific genetic variation.

SUMMARY OF THE INVENTION

The present invention overcomes a major deficiency in the art by providing tissue-specific genetic variation diagnosis methods relevant to the use of iPS cells, specifically, by providing specific disease-relevant cell types which may be challenging to isolate or obtain. In a first embodiment, there is provided a method for determining the presence of a tissue-specific genetic variation in a test subject relative to a selected control genetic structure, comprising: a) obtaining genetic material of a differentiated cell of a selected tissue, the cell having been prepared by differentiating an induced pluripotent stem (iPS) cells obtained by reprogramming a somatic cell of the test subject; and b) testing the genetic material of the differentiated cell to compare one or more genetic structure of the genetic material with one or more control genetic structures to determine the presence of such a genetic variation in cells of the tissue of the test subject. In certain embodiments, the selected tissue may be retina, neural tissue, or cardiac muscle tissue.

In certain aspects, the subject may have or be suspected of having a genetic abnormality or genetic disease. The genetic disease may be a tissue-specific disease with genetic defects difficult to characterize, such as a retinal disease. For retina disease characterization, specific retina cell types, such as a neural retina cell or a retina pigment epithelium (RPE) cell, could be provided by certain aspects of the present methods, specifically by differentiating iPS cells reprogrammed from a somatic cell derived from the test subject.

The genetic material of the differentiated cell, which may comprise nucleotides such as RNA or DNA, could be tested by various ways known in the art, such as nucleotide sequencing, e.g., RNA or DNA sequencing, or microarray analysis. The genetic structure may be primary nucleotide sequence, secondary structure, epigenetic structure, chromosome structure and the like. In further aspects of the invention, the genetic structure of the differentiated cell may be represented by an expression profile, which may reflect the functional consequences of transcriptional control regions within DNA sequences, which are not apparent from simple nucleotides sequencing alone.

Certain aspects of the present methods may be used to identify genetic variation, which may be variation of one or more coding sequences, or variation of one or more non-coding sequences, such as gene regulatory elements. The genetic variation determined by those steps above could be any types of mutations, such as deletion, insertion, mismatches, translocation, duplication, inversion, loss of heterozygosity; or polymorphism, such as single-nucleotide polymorphism (SNP); or represented by differential expression. Also the genetic variation can be a difference in transcript abundance resulting from differences in the functioning of expression control elements in the patient tissues.

The present methods may be particularly useful for determining the presence of genetic variation such as polymorphisms in non-coding regions, like introns or regulatory regions including, but are not limited to, promoters, enhancers, silencers, responsive elements, or regulatory sequences on RNA, such as 5'- or 3'-UTR (untranslated regions), or any uncharacterized regulatory elements. The genetic variation may also comprise variation in non-coding RNA, such as microRNA, or epigenetic variation, such as variation in modification of the genetic structure, e.g., methylation.

To determine the presence of such a genetic variation, a selected control gene structure may be used, such as one without the selected genetic variation. In a certain aspect, the control gene structure may be comprised in genetic material from a normal tissue, preferentially such a normal tissue may be from a control subject such as sibling or other family member of the test subject. The control subject may not have the genetic variation, especially in the tissue type of the selected tissue of the test subject. In a further aspect, the control gene structure may be comprised in genetic material, wherein the genetic material is from a selected normal cell prepared by differentiating an iPS cell obtained by reprogramming a normal somatic cell of a control subject, such as a subject who does not have the genetic variation. Preferably, the selected normal cell or the normal tissue may be of the same tissue type as the selected tissue of the test subject for comparison of tissue-specific genetic structure. In certain aspects, the control subject may be a family member related to the test subject.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

I. Introduction

The present disclosure, according to certain embodiments, is generally directed to methods for determining tissue-specific genetic variation by testing genetic material of specific cell types that may be derived from induced pluripotent stem cells. The genetic material may comprise any nuclear (chromosomal, DNA, RNA, etc.) and cytoplasmic (e.g., mitochondrial, proteins) material that could play a fundamental role in determining the nature of cell substances, cell structures, and/or cell effects. The genetic variation to be determined may include, for example, genetic defects or genetic polymorphism.

Genetic defects, which may result in a disease or disorder that is inherited genetically, comprise abnormalities in genetic structures, such as an absent or defective gene or a chromosomal aberration. Those genetic defects determined by certain aspects of the present invention could be applied for genetic disease diagnosis or even therapy.

Genetic polymorphism in specific tissue or cell types may also be determined by certain aspects of the present methods. For example, genetic polymorphism refers to the occurrence of more than one allele or genetic marker at the same locus, with the least frequent allele or marker occurring more frequently than can be accounted for by mutation alone. Genetic polymorphisms may include Single Nucleotide Polymorphisms (SNPs); Restriction Fragment Length Polymorphisms (RFLPs); Copy Number Polymorphisms; polymorphisms in transcription or expression, such as variation in RNA levels, timing or tissue distribution; polymorphisms in non-coding regions, including introns and regulatory elements, such as promoters, silencers, enhancers, responsive elements, transcription factors, untranslated regions, or non-coding RNA; trinucleotide repeat polymorphisms, for example, the number, dynamics and/or distribution of trinucleotides, such as CAG repeats; polymorphisms in epigenetic status, for example, methylation states; differential sensitivity to metabolism changes, growth factors (e.g., insulin), chemical or pharmaceutical agents, therapeutic procedures or treatments, or the like; susceptibility to a disease or disorder; variation in drug response, metabolism or toxicity, etc. For example, determination of genetic polymorphisms may be helpful for disease diagnosis or prognosis for their correlation to the occurrence of genetic defects or carrier status.

In certain aspects, genetic material testing may comprise determining polymorphism of RNA expression or sequence of the specific cell types. The cell-specific RNA characterization may be advantageous in yielding information that even complete DNA genome sequencing or complete what proteomics sequencing cannot yield. For example, as the functional consequences of variations in DNA control regions are not yet well understood, examining the RNA in the target tissue or cell types (whole transcriptome analysis) may be able to identify functional variations in the regulatory elements or regions that could not be identified by having an entire genome sequence sequenced and may provide information unavailable by whole genome sequencing. Particularly, gene expression level (e.g., transcription) is quantitative measure that is directly linked to genetic variation and can usually represent polymorphisms in regulatory elements. If a polymorphism or mutation in the regulatory elements is related to a tissue-specific disease or abnormality, it may be represented by changes in the RNA expression levels, localization, timing, or relative levels of spliced variants in the relevant tissue. RNA sequencing of the specific cell types may also reveal the specific variation much faster than DNA sequencing, as the inventors specifically examine the genetic material related to that cell type without requiring whole genome DNA sequences. This analysis would be best done in side-by-side comparison to unaffected siblings, to have the greatest chance of identifying the transcript differences associated with the disease condition.

The present invention could be a prelude to treating the tissue-specific disease by transplantation of differentiated cells derived from genetically corrected iPS cells, or a diagnostic of tissue- or cell-specific genetic variation alone. Additionally, certain aspects of this invention dramatically reduce the complexity of the identification of the genetic cause or the genetic marker for uncharacterized genetic disorders, since the inventors may start with the polymorphisms represented by difference between the control and test subject expression profiles rather than the whole genome or transcriptome.

II. Genetic Variation and Genetic Disease

Certain aspects provide methods to determine the presence of genetic variation, which may provide diagnosis of genetic diseases or abnormality. Genetic variation may play a key role in shaping phenotypic diversity amongst individuals, wherein the underlying mechanisms may include polymorphisms or abnormalities that alter protein coding sequences or changes in regulatory sequences that affect the function or expression of a gene or related gene networks. Genetic variation may result from the presence of different genotypes in the population and be associated with, render susceptibility to, or be the underlying cause for genetic disease or abnormality.

Genetic diseases may be caused by germ-line mutations that, despite tissue-wide presence, often lead to tissue-specific pathology, or abnormality in operation of regulatory elements, which may also have a tissue-specific phenotype.

A. Genetic Variation

Genetic variation may influence gene expression in specific tissue or cell types. In certain aspects of the present methods, by associating tissue or cell-specific expression with genetic structure, genetic variation could be identified or determined. For example, genetic variation may include polymorphisms such as single nucleotide polymorphisms (SNPs), which are DNA sequence variations occurring when a single nucleotide—A, T, C, or G—in the genome (or other shared sequence) differs between members of a species (or between paired chromosomes in an individual). Analysis of diploid sequences has also shown that non-SNP variation accounts for much more human genetic variation than single nucleotide diversity. This non-SNP variation includes copy number variation and may result from deletions, inversions, insertions and duplications. It is estimated that approximately 0.4% of the genomes of unrelated people typically differ with respect to copy number.

Some of the polymorphisms may be in non-coding regions of the genome while some may reside in the coding regions, for example, polymorphisms in regulatory regions or elements, or exonic variants altering transcript stability or splicing.

Genetic variation may include genetic regulatory polymorphisms acting in cis by changing the protein coding sequence or at the level of RNA: affecting transcription (activation or inhibition through regulatory sites or structure of regulatory elements), mRNA processing, pre-mRNA splicing, exonic splicing enhancers (ESEs), exon skipping, mRNA stability, mRNA trafficking, or regulatory RNAs. Epigenetic variation may mimic regulatory polymorphisms to some extent (Johnson et al., 2005).

Polymorphisms in regulatory regions or elements may be one of the key primary effects contributing to phenotypic variation in humans and thus important for molecular analysis of human phenotypic variation, some of which may be linked to genetic disorders.

For example, there is growing evidence that regulatory polymorphisms play an important role in the determination of individual susceptibility to complex disease traits (Knight 2005). Such regulatory polymorphisms include, but are not limited to, variation at the Variable Number Tandem Repeat (i.e., VNTR) of INS, encoding insulin, in type 1 diabetes; polymorphism of CTLA4, encoding cytotoxic T lymphocyte antigen, in autoimmune disease; polymorphism of Duffy binding protein in malaria; polymorphism of CCR5, encoding chemokine receptor 5, in HIV-1 infection. Genetic variation may also operate at other levels of control of gene expression and the modulation of splicing at PTPRC, encoding protein tyrosine phosphatase receptor-type C, and of translational efficiency at F12, encoding factor XII.

B. Genetic Disorders

A genetic disease (i.e., genetic disorder) is an illness caused by abnormalities in genes or chromosomes, or in gene regulatory elements. Abnormalities can range from a small mutation in a single gene to the addition or subtraction of an entire chromosome or set of chromosomes. Some diseases, such as cancer, are due in part to genetic disorders and also in part caused by environmental factors. Some types of recessive gene disorders confer an advantage in the heterozygous state in certain environments. A haploid cell has only one set of chromosomes. A diploid cell has two sets of chromosomes. In human, the somatic cells are diploid, and the gametes are haploid.

The range of genetic diseases is so broad in nature that affected individuals can be found in virtually all medical practices. Simply put, genetic blueprint influences health from the moment of conception until death. Based on a population study of genetic disorders apparent by the age of 25 years (Baird et al., 1988), about 0.4% of the population have a single gene (Mendelian) disorder, 0.2% have a chromosomal abnormality and 4.6% have a multifactorial condition. Another 0.1% have an obvious genetic abnormality of unknown inheritance, and 0.3% have congenital problems that are not genetic in nature. A single gene disorder is the result of a single mutated gene. There are estimated to be over 4000 human diseases caused by single gene defects. Single gene disorders can be passed on to subsequent generations in several ways. Genomic imprinting and uniparental disomy, however, may affect inheritance patterns. The divisions between recessive and dominant types are not "hard and fast" although the divisions between autosomal and X-linked types are (since the latter types are distinguished purely based on the chromosomal location of the gene). For example, achondroplasia is typically considered a dominant disorder, but children with two genes for achondroplasia have a severe skeletal disorder that achondroplasics could be viewed as carriers of. Sickle-cell anemia is also considered a recessive condition, but heterozygous carriers have increased immunity to malaria in early childhood, which could be described as a related dominant condition.

Only one mutated copy of the gene will be necessary for a person to be affected by an autosomal dominant disorder. Each affected person usually has one affected parent. There is a 50% chance that a child will inherit the mutated gene. Conditions that are autosomal dominant often have low penetrance, which means that although only one mutated copy is needed, a relatively small proportion of those who inherit that mutation go on to develop the disease. Examples of this type of disorder are Huntington's disease, Neurofibromatosis 1, Marfan Syndrome, Hereditary nonpolyposis colorectal cancer, and Hereditary multiple exostoses, which is a highly penetrant autosomal dominant disorder. Birth defects are also called congenital anomalies.

Two copies of the gene must be mutated for a person to be affected by an autosomal recessive disorder. An affected person usually has unaffected parents who each carry a single copy of the mutated gene (and are referred to as carriers). Two unaffected people who each carry one copy of the mutated gene have a 25% chance with each pregnancy of having a child affected by the disorder. Examples of this type of disorder are cystic fibrosis, sickle-cell disease (also partial sickle-cell disease), Tay-Sachs disease, Niemann-Pick disease, spinal muscular atrophy, and Dry (otherwise known as "rice-brand") earwax.

X-linked dominant disorders are caused by mutations in genes on the X chromosome. Only a few disorders have this inheritance pattern, with a prime example being X-linked hypophosphatemic rickets. Males and females are both affected in these disorders, with males typically being more severely affected than females. Some X-linked dominant conditions such as Rett syndrome, Incontinentia Pigmenti type 2 and Aicardi Syndrome are usually fatal in males either in utero or shortly after birth, and are therefore predominantly seen in females. Exceptions to this finding are extremely rare cases in which boys with Klinefelter Syndrome (47, XXY) also inherit an X-linked dominant condition and exhibit symptoms more similar to those of a female in terms of disease severity. The chance of passing on an X-linked dominant disorder differs between men and women. The sons of a man with an X-linked dominant disorder will all be unaffected (since they receive their father's Y chromosome), and his daughters will all inherit the condition. A woman with an X-linked dominant disorder has a 50% chance of having an affected fetus with each pregnancy, although it should be noted that in cases such as Incontinentia Pigmenti only female offspring are generally viable. In addition, although these conditions do not alter fertility per se, individuals with Rett syndrome or Aicardi syndrome rarely reproduce.

X-linked recessive disorders are also caused by mutations in genes on the X chromosome. Males are more frequently affected than females, and the chance of passing on the disorder differs between men and women. The sons of a man with an X-linked recessive disorder will not be affected, and his daughters will carry one copy of the mutated gene. A woman who is a carrier of an X-linked recessive disorder (XRXr) has a 50% chance of having sons who are affected and a 50% chance of having daughters who carry one copy of the mutated gene and are therefore carriers. Examples of this type of disorder are Hemophilia A, Duchenne muscular dystrophy, red-green color blindness, Muscular dystrophy and Androgenetic alopecia.

Y-linked disorders are caused by mutations on the Y chromosome. Because males inherit a Y chromosome from their fathers, every son of an affected father will be affected. Because females inherit an X chromosome from their fathers, female offspring of affected fathers are never affected. Since the Y chromosome is relatively small and contains very few genes, there are relatively few Y-linked disorders. Often the symptoms include infertility, which may be circumvented with the help of some fertility treatments. Examples are Male Infertility and hypertrichosis pinnae.

Genetic disorders may also be complex, multifactorial or polygenic, this means that they are likely associated with the effects of multiple genes in combination with lifestyle and environmental factors. Multifactoral disorders include heart disease and diabetes. Although complex disorders often cluster in families, they do not have a clear-cut pattern of inheritance. This makes it difficult to determine a person's risk of inheriting or passing on these disorders. Complex disorders are also difficult to study and treat because the specific factors that cause most of these disorders have not yet been identified.

C. Consideration of Genetic Disorders or Abnormalities

The same considerations that go into adding a possible genetic disorder to a neonate's or child's differential diagnosis apply to adults. Is this disorder genetic or acquired? How significant is the genetic component versus the environmental component? What is the pattern of inheritance? Is there potential for other members of the patient's family to be affected presently or in the future? How can the diagnosis be confirmed? There are a few clues that will suggest a genetic diagnosis. The family history might point to a genetic disorder. A great many disorders of adult onset are dominant in nature. That is, a mutation in only one of a gene pair is necessary to produce a genetic problem. (This contrasts with recessive inheritance in which both genes of a pair must have a mutation.) Dominant genetic disorders are very likely to produce a family history, whereas recessive disorders are not. Unfortunately, some dominant conditions have a high new mutation rate, so your patient might well be the first case in the family. Alternatively, a positive family history may not have previously been appreciated, perhaps because of the small size of the family or dispersion of family members. Family members who carried a gene mutation may have died before they developed signs and symptoms, or a genetic diagnosis may have never previously been entertained despite the existence of affected relatives.

Pedigree analysis may be complicated by the phenomena of incomplete penetrance and variable expressivity (Harper, 1998). Incomplete penetrance means that some individuals may carry a genetic mutation but not express any signs and symptoms. Variable expressivity means that even though all affected members of the family have the same mutation, they may not have identical manifestations. Age of onset and severity of the condition may vary considerably.

When a disease occurs at a much younger age than one would normally expect, it suggests a possible genetic predisposition. For example, breast cancer in a 25-year-old is very unusual (Langston et al., 1996). Paired with a history of breast and ovarian cancer in close relatives, this is virtually diagnostic of a mutation to a BRCA gene (Haber, 1999).

Physicians should also consider a genetic cause in three additional circumstances: cases with multisystem involvement (e.g., the deafness and nephritis associated with Alport's syndrome (Flinter, 1997)), with a multifocal presentation (e.g., the multiplicity of polyps throughout the colon diagnostic of familial adenomatous polyposis (Midgley and Kerr, 1999)) or with an unusual combination of events (e.g., early onset osteoporosis and conductive hearing loss may be indicative of osteogenesis imperfecta (Byers and Steiner, 1992)).

D. Genetic Eye Disorders

In particular, the present methods may be used to determine genetic variation or identify novel genetic defects in specific retina cells types differentiated from iPS cells, which may be derived from a patient having or suspected of having a genetic eye disorder, such as retinitis pigmentosa.

Retinitis pigmentosa (RP) is a group of genetic eye disorders. In the progression of symptoms for RP, night blindness generally precedes tunnel vision by years or even decades. Many people with RP do not become legally blind until their 40s or 50s and retain some sight all their life. Others go completely blind from RP, in some cases as early as childhood. Progression of RP is different in each case.

RP is a type of progressive retinal dystrophy, a group of inherited disorders in which abnormalities of the photoreceptors (rods and cones) or the retinal pigment epithelium (RPE) of the retina lead to progressive visual loss. Affected individuals first experience defective dark adaptation or nyctalopia (night blindness), followed by reduction of the peripheral visual field (known as tunnel vision) and, sometimes, loss of central vision late in the course of the disease.

The diagnosis of retinitis pigmentosa relies upon documentation of progressive loss in photoreceptor function by electroretinography (ERG) and visual field testing. The mode of inheritance of RP is determined by family history. At least 35 different genes or loci are known to cause "nonsyndromic RP" (RP that is not the result of another disease or part of a wider syndrome).

There are multiple genes that, when mutated, can cause the Retinitis pigmentosa phenotype. In 1989, a mutation of the gene for rhodopsin, a pigment that plays an essential part in the visual transduction cascade enabling vision in low-light conditions, was identified. Since then, more than 100 mutations have been found in this gene, accounting for 15% of all types of retinal degeneration. Most of those mutations are missense mutations and inherited mostly in a dominant manner. The rhodopsin gene encodes a principal protein of photoreceptor outer segments. Studies show that mutations in this gene are responsible for approximately 25% of autosomal dominant forms of RP.

Mutations in four pre-mRNA splicing factors are known to cause autosomal dominant retinitis pigmentosa. These are PRPF3, PRPF8, PRPF31 and PAP1. These factors are ubiquitously expressed and it is still a puzzle as to why defects in a ubiquitous factor should only cause disease in the retina.

Up to 150 mutations have been reported to date in the opsin gene associated with the RP since the Pro23His mutation in the intradiscal domain of the protein was first reported in 1990. These mutations are found throughout the opsin gene and are distributed along the three domains of the protein (the intradiscal, transmembrane, and cytoplasmic domains). One of the main biochemical causes of RP in the case of rhodopsin mutations is protein misfolding, and molecular chaperones have also been involved in RP. It was found that the mutation of codon 23 in the rhodopsin gene, in which proline is changed to histidine, accounts for the largest fraction of rhodopsin mutations in the United States. Several other studies have reported other mutations which also correlate with the disease. These mutations include Thr58Arg, Pro347Leu, Pro347Ser, as well as deletion of Ile-255. In 2000, a rare mutation in codon 23 was reported causing autosomal dominant retinitis pigmentosa, in which proline changed to alanine However, this study showed that the retinal dystrophy associated with this mutation was characteristically mild in presentation and course. Furthermore, there was greater preservation in electroretinography amplitudes than the more prevalent Pro23His mutation.

III. Molecular Diagnostics

While new molecular diagnostic tests are being developed and the range of available tests is increasing rapidly, the vast majority of genetic disorders still lack a genetic test with uncharacterized genetic basis. Certain aspects of the present methods provide tissue or cell-specific analysis of differences in genetic structure comprising genomic structure, which may be represented by expression profile between cells derived from a test subject and a normal cell, for example, a normal cell of the same cell or tissue type.

A genetic test is the analysis of human DNA, RNA, chromosomes, proteins or certain metabolites in order to detect alterations related to a heritable disorder. This can be accomplished by directly examining the DNA or RNA that makes up a gene (direct testing), looking at markers co-inherited with a disease-causing gene (linkage testing), assaying certain metabolites (biochemical testing), or examining the chromosomes (cytogenetic testing). Genetic testing is often the best way to confirm a diagnosis in a patient with signs or symptoms suggestive of a genetic disease. The technique chosen depends on both the clinical question and the predictive value of the available tests.

A. RNA Sequencing

RNA is less stable in the cell, and also more prone to nuclease attack experimentally. As RNA is generated by transcription from DNA, the information is already present in the cell's DNA. However, it is sometimes desirable to sequence RNA molecules. In particular, in Eukaryotes RNA molecules are not necessarily co-linear with their DNA template, as introns are excised. To sequence RNA, the usual method is first to reverse transcribe the sample to generate DNA fragments. This can then be sequenced as DNA sequencing.

Microarray technology and varied multiplex amplification methods have shown that RNA is valid as a target for routine molecular diagnostics and for future point-of-care testing. Detection of genetic defects in RNA profile in tissue-specific diseases or disorders may lend more accuracy and objectivity and provide more information to the diagnostic process than DNA-based detection methods. The main challenge using protein as a target for routine diagnostics has been low sensitivity, reproducibility and specificity. However, RNA and not DNA as a target for routine diagnostics may give the information of clinical activity, regulation or processes in addition to higher or equal sensitivity, reproducibility and specificity compared to DNA as target. For more than 10 years new methods of isolation, purification and stabilization of mRNA has been developed for routine diagnostics making the RNA very much suited as a marker for development of new diagnostics methods and even drugs.

The four aspects that are relevant to molecular diagnostics or gene function are levels of RNA expression, tissue specificity of RNA expression, timing of RNA expression, and the primary sequence of the RNA. By just examining the RNA in the target tissue or cells with certain aspects of the present invention, it will be much easier to identify a specific defect than having an entire genomic sequence, as the functional consequences of changes in DNA control regions are not yet understood, but such differences would impact RNA levels, timing, or tissue distribution.

In certain aspects, RNA sequencing may be used to identify the genetic defect in the specific cell types derived from iPS cells. RNA-Seq, also called "Whole Transcriptome Shotgun Sequencing" ("WTSS") and "a revolutionary tool for transcriptomics," refers to the use of High-throughput sequencing technologies to sequence cDNA in order to get information about a sample's RNA content, a technique that is quickly becoming invaluable in the study of genetic diseases (Denoeud et al., 2008). Thanks to the deep coverage and base level resolution provided by next-generation sequencing instruments, RNA-Seq provides efficient ways to measure transcriptome data experimentally, and to get information such as how different alleles of a gene are expressed, detect post-transcriptional mutations or identifying gene fusions.

B. Microarray

A DNA microarray is a multiplex technology used in molecular biology and in medicine. It consists of an arrayed series of thousands of microscopic spots of DNA oligonucleotides, called features, each containing picomoles of a specific DNA sequence. This can be a short section of a gene or other DNA element that are used as probes to hybridize a cDNA or cRNA sample (called target) under high-stringency conditions. Probe-target hybridization is usually detected and quantified by detection of fluorophore-, silver-, or chemiluminescence-labeled targets to determine relative abundance of nucleic acid sequences in the target.

In standard microarrays, the probes are attached to a solid surface by a covalent bond to a chemical matrix (via epoxy-silane, amino-silane, lysine, polyacrylamide or others). The solid surface can be glass or a silicon chip, in which case they are commonly known as gene chip or colloquially Affy chip when an Affymetrix chip is used. Other microarray platforms, such as Illumina, use microscopic beads, instead of the large solid support. DNA arrays are different from other types of microarray only in that they either measure DNA or use DNA as part of its detection system.

DNA microarrays can be used to measure changes in expression levels, to detect single nucleotide polymorphisms (SNPs), in genotyping or in resequencing mutant genomes for determination of genetic variation in certain aspects. More specifically, DNA microarrays can be used to detect DNA (as in comparative genomic hybridization), or detect RNA (most commonly as cDNA after reverse transcription) that may or may not be translated into proteins. The process of measuring gene expression via cDNA is called expression analysis or expression profiling. In further aspects, the genetic defect in the specific cell types derived from iPS cells may be identified by gene expression profiling, the measurement of the activity (the expression) of thousands of genes at once, to create a global picture of cellular function. Many experiments of this sort measure an entire genome simultaneously, that is, every gene present in a particular cell. Examples of gene expression profiling include, but are not limited to, DNA microarray, SAGE, or qPCR.

DNA microarray technology measures the relative activity of previously identified target genes. This can be a short section of a gene or other DNA element that are used as probes to hybridize a cDNA or cRNA sample (called target) under high-stringency conditions. Sequence based techniques, like serial analysis of gene expression (SAGE, SuperSAGE) may be also used for gene expression profiling. SuperSAGE is especially accurate and can measure any active gene, not just a predefined set. Real-time polymerase chain reaction, also called quantitative real time polymerase chain reaction (Q-PCR/qPCR) or kinetic polymerase chain reaction, is a laboratory technique based on the polymerase chain reaction, which is used to amplify and simultaneously quantify a targeted cDNA molecule. It enables both detection and quantification (as absolute number of copies or relative amount when normalized to cDNA input or additional normalizing genes) of a specific sequence in a cDNA sample.

C. Linkage Analysis

Regarding families with a genetic disorder in which the mutations cannot be located, if the gene is cloned or its location in the genome is identified by genetic mapping, a limited form of genetic testing can be offered that is based on linkage analysis. This involves the use of polymorphic DNA or RNA sequences that are closely linked to or found within the gene to track the mutant sequence through the family. The technique can be used if two or more generations of affected family members are available for study and may need extensive analysis of the family for informative markers. This approach may be also limited by potential errors due to genetic recombination or genetic heterogeneity (if more than one gene locus is potentially responsible for the same disorder in different families). Despite these limitations, linkage-based testing has been very useful for counseling families with genetic diseases such as Duchenne's muscular dystrophy, hemophilia, spinal muscular atrophy, and many other disorders.

D. Polymorphism identification methods

Measurement of sequence variants, primarily single nucleotide polymorphisms (SNPs), provides the fundamental units for linking genetic sequence to traits. Most genes harbor multiple sequence variations (e.g., SNPs, repeats, indels) showing a broad range of frequencies and linkage disequilibrium among them. Most polymorphisms are non-functional and may serve as markers for functional alleles. In addition to using single polymorphisms, associations are also often made with the use of haplotypes, blocks of linked polymorphisms, that may demarcate trait-significant cis-regions of sequence. High-throughput SNP genotyping methods are now coming online, such as SNPlex, capable of screening thousands of SNP in many samples (Wenz, 2004). Such methods have been used to establish haplotype maps on a genome-wide basis, including genes involved in drug metabolism, at significant marker density (Kamatani et al., 2004).

In certain aspects of the present invention, mRNA expression measured by microarrays may be combined with genome-wide linkage analysis, taking the expression level of each gene as the measured phenotype restricted to specific tissue or cell type. Heritability of gene expression phenotypes can be explored through familial genotyping and transmission disequilibrium testing in nuclear families (Spielman & Ewens, 1996) or pedigree disequilibrium testing in larger pedigrees (Martin et al., 2000). Using target tissues (derived from iPS cells) from family members, this type of analysis is capable of distinguishing between cis- and trans-acting genetic factors and shows an abundance of functional genomic loci and a preponderance of trans-acting effects, as expected.

An alternative approach involves the analysis of allele specific expression in a relevant target tissue, which may also be prepared from iPS cells; each allele experiences its own regulation in the same cellular environment, with the other allele (for autosomal genes) serving as an internal control. As a result, the method controls for tissue conditions, trans-acting factors, and other environmental influences. Thus, SNPs in exonic and untranslated regions of message, can serve as markers for allele expression levels in individuals heterozygous for these markers. Taking the human solute carrier family 15 (H+/peptide transporter), member 2 gene (hPepT2) as one example, it has been recently described a method for allele-specific measurement of mRNA expression through primer extension incorporation of fluorescent dideoxy-nucleotide terminating probes after RT-PCR amplification (Pinsonneault et al., 2004). Significant differences in the relative abundance of each allele in mRNA from kidney tissues demonstrated the presence of functional cisacting factors. The primer extension reaction can be multiplexed (Bray et al., 2004) so that it will be possible to search for functional cis-acting polymorphisms in a large number of genes (Yan et al., 2002). Similar results can be achieved through methods employed on other platforms (Wojnowski & Brockmoller, 2004) including the use of matrix-assisted laser desorption/ionization time-of-flight spectroscopy (MALDI-TOF; Ding et al., 2004) and allele-specific RT-PCR methodologies (Zhang et al., 2004). These techniques may be extended to unprocessed heterogeneous nuclear RNA (hnRNA) if exonic and untranslated markers are unavailable and hnRNA is abundant enough in the target samples (Hirota et al., 2004).

IV. Stem Cells

In certain embodiments of the invention, there are disclosed methods of using induced pluripotent stem cells (iPS cells) for determination of tissue-specific genetic variation. Those iPS cells may be made by reprogramming somatic cells and could be identical to embryonic stem cells in various aspects as described below. Understanding of embryonic stem cell characteristics could help select induced pluripotent stem cells. Reprogramming factors known from stem cell reprogramming studies could be used for these novel methods. It is further contemplated that these induced pluripotent stem cells could be potentially used to replace embryonic stem cells for therapeutics and research applications due to the ethics hurdle to use the latter.

A. Stem Cells

Stem cells are cells found in most, if not all, multi-cellular organisms. They are characterized by the ability to renew themselves through mitotic cell division and differentiating into a diverse range of specialized cell types. The two broad types of mammalian stem cells are: embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues.

As stem cells can be grown and transformed into specialized cells with characteristics consistent with cells of various tissues such as muscles or nerves through cell culture, their use in medical therapies has been proposed. In particular, embryonic cell lines, autologous embryonic stem cells generated through therapeutic cloning, and highly plastic adult stem cells from the umbilical cord blood or bone marrow are touted as promising candidates. Most recently, the reprogramming of adult cells into induced pluripotent stem cells has enormous potential for replacing embryonic stem cells.

B. Embryonic Stem Cells

Embryonic stem cell lines (ES cell lines) are cultures of cells derived from the epiblast tissue of the inner cell mass (ICM) of a blastocyst or earlier morula stage embryos. A blastocyst is an early stage embryo—approximately four to five days old in humans and consisting of 50-150 cells. ES cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta.

Nearly all research to date has taken place using mouse embryonic stem cells (mES) or human embryonic stem cells (hES). Both have the essential stem cell characteristics, yet they require very different environments in order to maintain an undifferentiated state. Mouse ES cells may be grown on a layer of gelatin and require the presence of Leukemia Inhibitory Factor (LIF). Human ES cells could be grown on a feeder layer of mouse embryonic fibroblasts (MEFs) and often require the presence of basic Fibroblast Growth Factor (bFGF or FGF-2). Without optimal culture conditions or genetic manipulation (Chambers et al., 2003), embryonic stem cells will rapidly differentiate.

A human embryonic stem cell may be also defined by the presence of several transcription factors and cell surface proteins. The transcription factors Oct4, Nanog, and Sox2 form the core regulatory network that ensures the suppression of genes that lead to differentiation and the maintenance of pluripotency (Boyer et al., 2005). The cell surface antigens most commonly used to identify hES cells include the glycolipids SSEA3 and SSEA4 and the keratan sulfate antigens Tra-1-60 and Tra-1-81.

After twenty years of research, there are no approved treatments or human trials using embryonic stem cells. ES cells, being pluripotent cells, require specific signals for correct differentiation—if injected directly into the body, ES cells will differentiate into many different types of cells, causing a teratoma. Differentiating ES cells into usable cells while avoiding transplant rejection are just a few of the hurdles that embryonic stem cell researchers still face. Many nations currently have moratoria on either ES cell research or the production of new ES cell lines. Because of their combined abilities of unlimited expansion and pluripotency, embryonic stem cells remain a theoretically potential source for regenerative medicine and tissue replacement after injury or disease. However, one way to circumvent these issues is to induce pluripotent status in somatic cells by direct reprogramming.

C. Induced pluripotent Stem Cells and Reprogramming Factors

Induced pluripotent stem cells, commonly abbreviated as iPS cells or iPSCs, are a type of pluripotent stem cell artificially derived from a non-pluripotent cell, typically an adult somatic cell. Induced pluripotent stem cells are believed to be identical to natural pluripotent stem cells, such as embryonic stem cells in many respects, such as in terms of the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

IPS cells were first produced in 2006 (Takahashi et al., 2006) from mouse cells and in 2007 from human cells (Takahashi et al., 2007; Yu et al, 2007). This has been cited as an important advancement in stem cell research, as it may allow researchers to obtain pluripotent stem cells, which are important in research and potentially have therapeutic uses, without the controversial use of embryos.

The generation of iPS cells is crucial on the reprogramming factors used for the induction. The following factors or combination thereof could be used in the methods disclosed in the present invention. In certain aspects, nucleic acids encoding Sox and Oct (preferably Oct3/4) will be included into the reprogramming vector. For example, one or more reprogramming vectors may comprise expression cassettes encoding Sox2, Oct4, Nanog and optionally Lin28, or expression cassettes encoding Sox2, Oct4, Klf4 and optionally c-Myc, or expression cassettes encoding Sox2, Oct4, and optionally Esrrb, or expression cassettes encoding Sox2, Oct4, Nanog, Lin28, Klf4, c-Myc, and optionally SV40 Large T antigen. Nucleic acids encoding these reprogramming factors may be comprised in the same expression cassette, different expression cassettes, the same reprogramming vector, or different reprogramming vectors.

Oct4 and certain members of the Sox gene family (Sox1, Sox2, Sox3, and Sox15) have been identified as crucial transcriptional regulators involved in the induction process whose absence makes induction impossible. Additional genes, however, including certain members of the Klf family (Klf1, Klf2, Klf4, and Klf5), the Myc family (c-Myc, L-Myc, and N-Myc), Nanog, and Lin28, have been identified to increase the induction efficiency.

Oct4 (Pou5f1) is one of the family of octamer ("Oct") transcription factors, and plays a crucial role in maintaining pluripotency. The absence of Oct4 in Oct4$^+$ cells, such as blastomeres and embryonic stem cells, leads to spontaneous trophoblast differentiation, and presence of Oct4 thus gives rise to the pluripotency and differentiation potential of embryonic stem cells. Various other genes in the "Oct" family, including Oct4's close relatives, Oct1 and Oct6, fail to elicit induction, thus demonstrating the exclusiveness of Oct-4 to the induction process.

The Sox family of genes is associated with maintaining pluripotency similar to Oct4, although it is associated with multipotent and unipotent stem cells in contrast with Oct4, which is exclusively expressed in pluripotent stem cells. While Sox2 was the initial gene used for induction by Takahashi et al. (2006), Wernig et al. (2007), and Yu et al. (2007), other genes in the Sox family have been found to work as well in the induction process. Sox1 yields iPS cells with a similar efficiency as Sox2, and genes Sox3, Sox15, and Sox18 also generate iPS cells, although with decreased efficiency.

In embryonic stem cells, Nanog, along with Oct4 and Sox2, is necessary in promoting pluripotency. Therefore, it was surprising when Takahashi et al. (2006) reported that Nanog was unnecessary for induction although Yu et al. (2007) has reported it is possible to generate iPS cells with Nanog as one of the factors.

Lin28 is an mRNA binding protein expressed in embryonic stem cells and embryonic carcinoma cells associated with differentiation and proliferation. Thompson et al. demonstrated it is a factor in iPS generation, although it is unnecessary.

Klf4 of the Klf family of genes was initially identified by Takahashi et al. (2006) and confirmed by Wernig et al. (2007) as a factor for the generation of mouse iPS cells and was demonstrated by Takahashi et al. (2007) as a factor for generation of human iPS cells. However, Yu et al. (2007) reported that Klf4 was unnecessary for generation of human iPS cells and in fact failed to generate human iPS cells. Klf2 and Klf4 were found to be factors capable of generating iPS cells, and related genes Klf1 and Klf5 did as well, although with reduced efficiency.

The Myc family of genes are proto-oncogenes implicated in cancer. Takahashi et al. (2006) and Wernig et al. (2007) demonstrated that c-Myc is a factor implicated in the generation of mouse iPS cells and Takahashi et al. (2007) demonstrated it was a factor implicated in the generation of human iPS cells. However, Yu et al. (2007) and Takahashi et al. (2007) reported that c-Myc was unnecessary for generation of human iPS cells. Usage of the "Myc" family of genes in induction of iPS cells is troubling for the eventuality of iPS cells as clinical therapies, as 25% of mice transplanted with c-Myc-induced iPS cells developed lethal teratomas. N-Myc and L-Myc have been identified to induce in the stead of c-myc with similar efficiency. SV40 large antigen may be used to reduce or prevent the cytotoxcity which may occur when c-Myc is expressed.

The reprogramming proteins used in the present invention can be substituted by protein homologs with about the same reprogramming functions. Nucleic acids encoding those homologs could also be used for reprogramming. Conservative amino acid substitutions are preferred--that is, for example, aspartic-glutamic as polar acidic amino acids; lysine/arginine/histidine as polar basic amino acids; leucine/isoleucine/methionine/valine/alanine/glycine/proline as non-polar or hydrophobic amino acids; serine/threonine as polar or uncharged hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide.

V. Reprogramming Factors Expression

In certain aspects of the present invention, iPS cells are maded from reprogramming somatic cells using reprogramming factors. The somatic cell in the present invention may be any somatic cell that can be induced to pluripotency, such as a fibroblast, a keratinocyte, a hematopoietic cell, a mesenchymal cell, a liver cell, a stomach cell, or a β cell. In a prefered aspect, T cells may be used as source of somatic cells for reprogramming (see U.S. Application No. 61/184,546, incorporated herein by reference).

Reprogramming factors may be expressed from expression cassettes comprised in one or more vectors, such as an integrating vector or an episomal vector. In a further aspect, reprogramming proteins could be introduced directly into somatic cells by protein transduction (see U.S. Application No. 61/172,079, incorporated herein by reference).

A. Integrating Vectors

IPS cells may be derived by transfection of certain nucleic acids or genes encoding reprogramming proteins into non-pluripotent cells, such as T cells, in the present invention. Transfection is typically achieved through integrating viral vectors in the current practice, such as retroviruses. Transfected genes may include the master transcriptional regulators Oct4 (Pouf51) and Sox2, although it is suggested that other genes enhance the efficiency of induction. After a critical period, small numbers of transfected cells may begin to become morphologically and biochemically similar to pluripotent stem cells, and could be isolated through morphological selection, doubling time, or through a reporter gene and antibiotic infection.

In November 2007, a milestone was achieved by creating iPS from adult human fibroblasts from two independent research teams' studies (Yu et al., 2007; Takahashi et al., 2007). With the same principle used earlier in mouse models, Takahashi et al. (2007) had successfully transformed human fibroblasts into pluripotent stem cells using the same four pivotal genes: Oct4, Sox2, Klf4, and c-Myc with a retroviral system but c-Myc is oncogenic. Yu et al. (2007) used Oct4, Sox2, NANOG, and a different gene LIN28 using a lentiviral system avoiding the use of c-Myc.

As described above, induction of pluripotent stem cells from human dermal fibroblasts has been achieved using retroviruses or lentiviral vectors for ectopic expression of reprogramming genes. Recombinant retroviruses such as the Moloney murine leukemia virus have the ability to integrate into the host genome in a stable fashion. They contain a reverse transcriptase which allows integration into the host genome. Lentiviruses are a subclass of Retroviruses. They are widely adapted as vectors thanks to their ability to integrate into the genome of non-dividing as well as dividing cells. The viral genome in the form of RNA is reverse-transcribed when the virus enters the cell to produce DNA, which is then inserted into the genome at a random position by the viral integrase enzyme.

B. Episomal vectors

These reprogramming methods may also make use of extra-chromosomally replicating vectors (i.e., episomal vectors), which are vectors capable of replicating episomally to make iPS cells essentially free of exogenous vector or viral elements (see U.S. Application No. 61/058,858, incorporated herein by reference; Yu et al., 2009). A number of DNA viruses, such as adenoviruses, Simian vacuolating virus 40 (SV40) or bovine papilloma virus (BPV), or budding yeast ARS (Autonomously Replicating Sequences)-containing plasmids replicate extra-chromosomally or episomally in mammalian cells. These episomal plasmids are intrinsically free from all these disadvantages (Bode et al., 2001) associated with integrating vectors. For example, a lymphotrophic herpes virus-based including or Epstein Barr Virus (EBV) as defined above may replicate extra-chromosomally and help deliver reprogramming genes to somatic cells.

For example, the plasmid-based approach used in the invention may extract robust elements necessary for the successful replication and maintenance of an EBV element-based system without compromising the system's tractability in a clinical setting as described in detail below. The essential EBV elements are OriP and EBNA-1 or their variants or functional equivalents. An additional advantage of this system is that these exogenous elements will be lost with time after being introduced into cells, leading to self-sustained iPS cells essentially free of exogenous elements.

The use of plasmid- or liposome-based extra-chromosomal vectors, e.g., oriP-based vectors, and/or vectors encoding a derivative of EBNA-1 permit large fragments of DNA to be introduced to a cell and maintained extra-chromosomally, replicated once per cell cycle, partitioned to daughter cells efficiently, and elicit substantially no immune response. In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Also other sources of episome-base vectors are contemplated, such as yeast ARS, adenovirus, SV40, or BPV.

To circumvent potential problems from viral gene delivery, two groups this year reported on a collaboration that has succeeded in transposon-based approaches for producing pluripotency in human cells without using viral vectors (Woltjen et al., 2009; Kaji et al., 2009). Stable iPS cells were produced in both human and mouse fibroblasts using virus-derived 2A peptide sequences to create a multicistronic vector incorporating the reprogramming factors, delivered to the cell by the piggyBac transposon vector. The 2A-linked reprogramming factors, not required in the established iPS cell lines, were then removed. These strategies could be similarly applied to reprogram T cell in certain aspects of the present invention.

C. Protein Transduction

One possible way to avoid introducing exogenous genetic modifications to target cells would be to deliver the reprogramming proteins directly into cells, rather than relying on the transcription from delivered genes. Previous studies have demonstrated that various proteins can be delivered into cells in vitro and in vivo by conjugating them with a short peptide that mediates protein transduction, such as HIV tat and poly-arginine. A recent study demonstrated that murine fibroblasts can be fully reprogrammed into pluripotent stem cells by direct delivery of recombinant reprogramming proteins (Zhou et al., 2009). More details of the methods for reprogramming cells with protein transduction have been disclosed in U.S. Application No. 61/172,079 incorporated herein by reference.

In certain aspects of the present invention, protein transduction domains could been used to introduce reprogramming proteins directly into T cells. Protein transduction could be a method for enhancing the delivery of reprogramming proteins into cells. For example, a region of the TAT protein which is derived from the HIV Tat protein can be fused to a target protein allowing the entry of the target protein into the cell. The advantages of using fusions of these transduction domains is that protein entry is rapid, concentration-dependent and appears to work with different cell types.

In a further aspect of the present invention, nuclear localization sequence may also be used to facilitate nuclear entry of reprogramming proteins. Nuclear localization signals (NLS) have been described for various proteins. The mechanism of protein transport to the nucleus is through the binding of a target protein containing a nuclear localization signal to alpha subunit of karyopherin. This is followed by transport of the target protein:karyopherin complex through the nuclear pore and into the nucleus. However, reprogramming proteins are often transcription factors which may have endogenous nuclear localization sequences. Therefore, nuclear localization sequences may not be necessary.

The direct introduction of reprogramming proteins into somatic cells may be used in the present invention, with reprogramming proteins operatively linked to a protein transduction domain (PTD), either by creating a fusion protein comprising such a domain or by chemically cross-linking the reprogramming protein and PTD via functional groups on each molecule.

Standard recombinant nucleic acid methods can be used to express one or more transducible reprogramming proteins used herein. In one embodiment, a nucleic acid sequence encoding the transducible protein is cloned into a nucleic acid expression vector, e.g., with appropriate signal and processing sequences and regulatory sequences for transcription and translation. In another embodiment, the protein can be synthesized using automated organic synthetic methods.

In addition, there have been several methods that may also help the transport of proteins into cells, one ore more of which can be used alone or in combination with the methods using the protein transduction domains, including, but not limited to, microinjection, electroporation, and the use of liposomes. Most of these methods may need a purified preparation of protein. Purification of recombinant proteins is often facilitated by the incorporation of an affinity tag into the expression construct, making the purification step fast and efficient.

VI. IPS Cell Selection, Culturing, and Differentiation

In certain aspects of the invention, after one or more reprogramming factors are introduced into somatic cells of a test subject, cells will be cultured for expansion (optionally selected for the presence of vector elements like positive selection or screenable marker to concentrate transfected cells). Reprogramming vectors may express reprogramming factors in these cells and replicate and partition along with cell division. Alternatively, reprogramming proteins could enter these cells and their progeny by replenishing medium containing the reprogramming proteins. These reprogramming factors will reprogram somatic cell genome to establish a self-sustaining pluripotent state, and in the meantime or after removal of positive selection of the presence of vectors, exogenous genetic elements will be lost gradually, or there is no need to add reprogramming proteins.

These induced pluripotent stem cells could be selected from progeny cells based on embryonic stem cell characteristics because they are expected to be substantially identical to pluripotent embryonic stem cells. An additional negative selection step could be also employed to accelerate or help selection of iPS cells essentially free of exogenous genetic elements by testing the absence of reprogramming vector DNA or using selection markers, such as reporters.

After iPS cells are selected or isolated, differentiation into specific cells types may be induced from iPS cells for determination of tissue-specific genetic variation. The specific cell types may be comprised in a selected tissue, such as retina.

A. IPS Cell Selection

The successfully generated iPSCs from previous studies were remarkably similar to naturally-isolated pluripotent stem cells (such as mouse and human embryonic stem cells, mESCs and hESCs, respectively) in the following respects, thus confirming the identity, authenticity, and pluripotency of iPSCs to naturally-isolated pluripotent stem cells. Thus, induced pluripotent stem cells generated from the methods disclosed in this invention could be selected based on one or more of following embryonic stem cell characteristics.

i. Cellular Biological Properties

Morphology: iPSCs are morphologically similar to ESCs. Each cell may have round shape, dual nucleoli or large nucleolus and scant cytoplasm. Colonies of iPSCs could be also similar to that of ESCs. Human iPSCs form sharp-edged, flat, tightly-packed colonies similar to hESCs and mouse iPSCs form the colonies similar to mESCs, less flatt and more aggregated colonies than that of hESCs.

Growth properties: Doubling time and mitotic activity are cornerstones of ESCs, as stem cells must self-renew as part of their definition. iPSCs could be mitotically active, actively self-renewing, proliferating, and dividing at a rate equal to ESCs.

Stem Cell Markers: iPSCs may express cell surface antigenic markers expressed on ESCs. Human iPSCs expressed the markers specific to hESC, including, but not limited to, SSEA-3, SSEA-4, TRA-1-60, TRA-1-81, TRA-2-49/6E, and Nanog. Mouse iPSCs expressed SSEA-1 but not SSEA-3 nor SSEA-4, similarly to mESCs.

Stem Cell Genes: iPSCs may express genes expressed in undifferentiated ESCs, including Oct4, Sox2, Nanog, GDF3, REX1, FGF4, ESG1, DPPA2, DPPA4, and hTERT.

Telomerase Activity: Telomerases are necessary to sustain cell division unrestricted by the Hayflick limit of ~50 cell divisions. hESCs express high telomerase activity to sustain self-renewal and proliferation, and iPSCs also demonstrate high telomerase activity and express hTERT (human telomerase reverse transcriptase), a necessary component in the telomerase protein complex.

Pluripotency: iPSCs will be capable of differentiation in a fashion similar to ESCs into fully differentiated tissues.

Neural Differentiation: iPSCs could be differentiated into neurons, expressing βIII-tubulin, tyrosine hydroxylase, AADC, DAT, ChAT, LMX1B, and MAP2. The presence of catecholamine-associated enzymes may indicate that iPSCs, like hESCs, may be differentiable into dopaminergic neurons. Stem cell-associated genes will be downregulated after differentiation.

Cardiac Differentiation: iPSCs could be differentiated into cardiomyocytes that spontaneously begin beating. Cardiomyocytes express cTnT, MEF2C, MYL2A, MYHCβ, and NKX2.5. Stem cell-associated genes will be downregulated after differentiation.

Teratoma Formation: iPSCs injected into immunodeficient mice may spontaneously form teratomas after certain time, such as nine weeks. Teratomas are tumors of multiple lineages containing tissue derived from the three germ layers endoderm, mesoderm and ectoderm; this is unlike other tumors, which typically are of only one cell type. Teratoma formation is a landmark test for pluripotency.

Embryoid Body: hESCs in culture spontaneously form ball-like embryo-like structures termed "embryoid bodies," which consist of a core of mitotically active and differentiating hESCs and a periphery of fully differentiated cells from all three germ layers. iPSCs may also form embryoid bodies and have peripheral differentiated cells.

Blastocyst Injection: hESCs naturally reside within the inner cell mass (embryoblast) of blastocysts, and in the embryoblast, differentiate into the embryo while the blastocyst's shell (trophoblast) differentiates into extraembryonic tissues. The hollow trophoblast is unable to form a living embryo, and thus it is necessary for the embryonic stem cells within the embryoblast to differentiate and form the embryo. iPSCs injected by micropipette into a trophoblast to generate a blastocyst transferred to recipient females, may result in chimeric living mouse pups: mice with iPSC derivatives incorporated all across their bodies with 10%-90 and chimerism.

ii. Epigenetic reprogramming

Promoter Demethylation: Methylation is the transfer of a methyl group to a DNA base, typically the transfer of a methyl group to a cytosine molecule in a CpG site (adjacent cytosine/guanine sequence). Widespread methylation of a gene interferes with expression by preventing the activity of expression proteins or recruiting enzymes that interfere with expression. Thus, methylation of a gene effectively silences it by preventing transcription. Promoters of pluripotency-associated genes, including Oct4, Rex1, and Nanog, may be demethylated in iPSCs, showing their promoter activity and the active promotion and expression of pluripotency-associated genes in iPSCs.

Histone Demethylation: Histones are compacting proteins that are structurally localized to DNA sequences that can effect their activity through various chromatin-related modifications. H3 histones associated with Oct/4, Sox2, and Nanog may be demethylated to activate the expression of Oct4, Sox2, and Nanog.

B. Culturing of iPS cells

After somatic cells are introduced with reprogramming factors using the disclosed methods, these cells may be cultured in a medium sufficient to maintain the pluripotency. Culturing of induced pluripotent stem (iPS) cells generated in this invention can use various medium and techniques developed to culture primate pluripotent stem cells, more specially, embryonic stem cells, as described in U.S. Pat. App. 20070238170 and U.S. Pat. App. 20030211603. It is appreciated that additional methods for the culture and maintenance of human pluripotent stem cells, as would be known to one of skill, may be used with the present invention.

In certain embodiments, undefined conditions may be used; for example, pluripotent cells may be cultured on fibroblast feeder cells or a medium which has been exposed to fibroblast feeder cells in order to maintain the stem cells in an undifferentiated state. Alternately, pluripotent cells may be cultured and maintained in an essentially undifferentiated state using defined, feeder-independent culture system, such as a TESR™ medium (Ludwig et al., 2006a; Ludwig et al., 2006b). Feeder-independent culture systems and media may be used to culture and maintain pluripotent cells. These approaches allow human embryonic stem cells to remain in an essentially undifferentiated state without the need for mouse fibroblast "feeder layers." As described herein, various modifications may be made to these methods in order to reduce costs as desired.

For example, like human embryonic stem (hES) cells, iPS cells can be maintained in 80% DMEM (Gibco #10829-018 or #11965-092), 20% defined fetal bovine serum (FBS) not heat inactivated (or human AB serum), 1% non-essential amino acids, 1 mM L-glutamine, and 0.1 mM β-mercaptoethanol. Alternatively, iPS cells can be maintained in serum-free medium, made with 80% Knock-Out DMEM (Gibco #10829-018), 20% serum replacement (Gibco #10828-028), 1% non-essential amino acids, 1 mM L-glutamine, and 0.1 mM β-mercaptoethanol. Just before use, human bFGF may be added to a final concentration of about 4 ng/mL (WO 99/20741) or zebrafish bFGF may be used instead as in the Examples.

Various matrix components may be used in culturing and maintaining human pluripotent stem cells. For example, collagen IV, fibronectin, laminin, and vitronectin in combination may be used to coat a culturing surface as a means of providing a solid support for pluripotent cell growth, as described in Ludwig et al. (2006a; 2006b), which are incorporated by reference in its entirety.

Matrigel™ may also be used to provide a substrate for cell culture and maintenance of human pluripotent stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture.

IPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5\text{-}10\times10^6$ cells into the rear leg muscles of 8-12 week old male SCID mice. Teratomas develop that demonstrate at least one cell type of each of the three germ layers.

C. Differentiation of iPS Cells

Various approaches may be used with the present invention to differentiate genetically iPS cells into specific cell lineages including, but not limited to, retina epithelium cells, neural retina cells, hematopoietic cells, myocytes (e.g., cardiomyocytes), neurons, fibroblasts and epidermal cells, and tissues or organs derived therefrom. Differentiation into retina cells may be an example.

The retinal pigment epithelium (RPE) is the pigmented cell layer just outside the neurosensory retina that nourishes retinal visual cells, and is firmly attached to the underlying choroid and overlying retinal visual cells. The RPE is composed of a single layer of hexagonal cells that are densely packed with pigment granules. The retinal pigment epithelium is involved in the phagocytosis of the outer segment of photoreceptor cells and it is also involved in the vitamin A cycle where it isomerizes all trans retinol to 11-cis retinal. The retinal pigment epithelium also serves as the limiting transport factor that maintains the retinal environment by supplying small molecules such as amino acid, ascorbic acid and D-glucose while remaining a tight barrier to choroidal blood borne substances. Homeostasis of the ionic environment is maintained by a delicate transport exchange system. When viewed from the outer surface, these cells are smooth and hexagonal in shape. When seen in section, each cell consists of an outer non-pigmented part containing a large oval nucleus and an inner pigmented portion which extends as a series of straight thread-like processes between the rods, this being especially the case when the eye is exposed to light.

The isolation of RPE cells from human patient may be technically challenging and complicated. In certain aspects of the present invention, RPE cells may be obtained by differentiation of iPS cells for genetic defect identification. For example, RPE cells can be differentiated by methods disclosed in WO 2008/129554, Osakada et al. (2008), Osakada et al. (2009), and Hirami et al. (2009). For example, human iPS cells could be dissociated into small clumps of cells and seeded in Petri dishes as suspension cultures with a serum-free medium (SFEB/DL) containing Wnt and Nodal antagonists. Under these conditions, iPS cells could form embryoid body-like aggregates. On day 20, aggregates may be plated onto glass slides coated with poly-D-lysine, laminin, and fibronectin for further RPE differentiation.

The iPS cells may also be differentiated into cardiac or blood cells in certain aspects. Exemplary methods of cardiac differentiation of iPS cells may include embryoid body (EB) methods (Zhang, et al., 2009), or OP9 stroma cell methods (Narazaki, et al., 2008), or growth factor/chemical methods (see U.S. Patent Publn. 20080038820, 20080226558, 20080254003 and 20090047739, all incorporated herein by reference in their entirety). Exemplary methods of hematopoietic differentiation of iPS cells may include, but are not limited to, methods disclosed by U.S. Application No. 61/088,054 and No. 61/156,304, both incorporated herein by reference in their entirety, or embryoid body (EB) based methods (Chadwick et al., 2003; Ng et al., 2005). Fibronectin differentiation methods may also be used for blood lineage differentiation, as exemplified in Wang et al., 2007.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

IPS cells are made from a patient diagnosed with retinitis pigmentosa. As a control, iPS cells are also made from the patient's family member, preferably a sibling, who is without retinitis pigmentosa. Human iPS cell lines are obtained by the lentiviral-mediated transduction of four transcription factors (OCT4, SOX2, NANOG and LIN28) as previously described (Yu et al., 2007). The iPS cells derived both from the patient and the sibling are maintained on matrigel™ and cultured in TESR™ medium.

A single cell suspension is made by incubating colonies in TrypLe, a recombinant trypsin-like enzyme (Invitrogen, Carlsbad, Calif.) at 37° C. for 7 minutes, washed twice with TESR™ medium containing the apoptosis inhibitor H1152 and soybean trypsin inhibitor, and resuspended in 0.5 ml of cold PBS containing H1152 and soybean trypsin inhibitor. The suspension cultures are seeded on a gelatin-coated dish with serum-free medium supplemented with 100 ng/ml Dkk-1, a Wnt antagonist and 500 ng/ml Lefty A, a Nodal antagonist for 18-20 days to form aggregates. The aggregates are then plated onto culture slides coated with poly- D-lysine, laminin, and fibronectin and incubated in differentiation medium (G-MEM (GIBCO) containing 10% KSR (Knock-out serum replacement), 0.1 mM nonessential amino acids, 1 mM sodium pyruvate, 0.1 mM 2-mercaptoethanol, 50 units/ml penicillin, and 50 µg/ml streptomycin). RPE cells are selected and enriched by polygonal morphology, pigmentation and molecular markers like RPE-65 and ZO-1, a tight junction marker.

Total RNA is extracted from the RPE cells using TRIZOL® reagent (Invitrogen) or TM-Reagent (Sigma). cDNA synthesis is carried out using Moloney murine leukemia virus reverse transcriptase (M-MLV RT) and random primers, according to the manufacturer's instructions (Promega Corporation, Madison, WI). Polymerase chain reaction (PCR) is carried out using standard protocols with Taq DNA Polymerase (Gibco-BRL). Q-PCR, cDNA sequencing and microarray are used to compare the RPE cells derived from the patient and the related normal family member to determine one or more genetic variation.

\* \* \*

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Appln. Ser. 61/058,858
U.S. Appln. Ser. 61/088,054
U.S. Appln. Ser. 61/156,304
U.S. Appln. Ser. 61/172,079
U.S. Appln. Ser. 61/184,546
U.S. Patent Publn. 20030211603
U.S. Patent Publn. 20070238170
U.S. Patent Publn. 20080038820
U.S. Patent Publn. 20080226558
U.S. Patent Publn. 20080254003
U.S. Patent Publn. 20090047739
Andrews et al., In: *Teratocarcinomas and Embryonic Stem Cells*, Robertson (Ed.), IRL Press, 207-246,1987.
Baird et al., *Am. J. Hum. Genet.*, 42:677-93, 1988.
Bode et al., *Gene Ther. Mol. Biol.*, 6:33-46, 2001.
Boyer et al., *Cell*, 122 (6):947-56, 2005.
Bray et al., *Mol. Psychiatry*, 9 (1);109-114, 2004.
Byers and Steiner, *Ann. Rev. Med.*, 43:269-82, 1992.
Chadwick et al., *Blood*, 102 (3):906-15, 2003.
Chambers et al., *Cell*, 113 (5):643-55, 2003.
Denoeud et al., *Genome Biol.*, 9 (12):R175, 2008.
Ding et al., *BMC Genet.*, 5 (1):8, 2004.
Evans, et al., In: *Cancer Principles and Practice of Oncology*, Devita et al. (Eds.), Lippincot-Raven, NY, 1054-1087, 1997.
Flinter, *J. Med. Genet.*, 34:326-30, 1997.
Haber, *J. Clin. Oncol.*, 17 (11):3367-70, 1999.
Harper, In: *Practical genetic counselling*, 5$^{th}$ Ed., Butterworth-Heinemann, Boston, 1998.
Hirami et al., *Neurosci Lett.*, 458 (3):126-31, 2009
Hirota et al., *Hum. Mol. Genet.*, 13 (23):2959-2969, 2004.
Johnson et al., *Pharmacology & Therapeutics*, 106: 19-38, 2005.
Kaji et al., *Nature*, 458, 771-775, 2009.
Kamatani et al., *Am. J. Hum. Genet.*, 75 (2):190-203, 2004.
Knight, *J Mol Med.*, 83 (2):97-109, 2005.
Langle-Rouault et al., *J. Virol.*, 72 (7):6181-6185, 1998.
Langston et al., *N. Engl. J. Med.*, 334 (3):137-42, 1996.
Levitskaya et al., *Proc. Natl. Acad. Sci. USA*, 94 (23):12616-12621, 1997.
Ludwig et al., *Nat. Biotechnol.*, 24 (2):185-187, 2006b.
Ludwig et al., *Nat. Methods*, 3 (8):637-46, 2006a.
Martin et al., *Am. J. Hum. Genet.*, 67 (1):146-154, 2000.
Midgley and Kerr, *Lanet.*, 353:391-9, 1999.
Narazaki et al., *Circulation*, 118 (5): 498-506, 2008.
Ng et al., *Development*, 132 (5):873-84, 2005.
Osakada et al., *Nat. Biotech.*, 26:215-224, 2008.
Osakada et al., *Nat. Protocols*, 4:811-824, 2009.
PCT Appln. WO 2008/129554
PCT Appln. WO 99/20741
Pinsonneault et al., *J. Pharmacol. Exp. Ther.*, 311 (3):1088-1098, 2004.
Spielman and Ewens, *Am. J. Hum. Genet.*, 59 (5):983-989, 1996.
Takahashi et al., *Cell*, 126 (4):663-676, 2006.
Takahashi et al., *Cell*, 131 (5):861-72, 2007.
Wang et al., *Nat. Biotechnol.*, 25 (3):317-8, 2007.
Wenz, In: *A novel high-throughput SNP genotyping system utilizing capillary electrophoresis detection platforms*, Applied Biosystems, CA, 2004.
Wernig et al., *Nature*, 448 (7151):318-24, 2007
Wojnowski and Brockmoller, *Pharmacogenetics*, 14 (4): 267-269, 2004.
Woltjen et al., *Nature*, 458, 766-770, 2009.
Yan et al., *Science*, 297 (5584):1143, 2002.
Yu et al., *Science*, 318:1917-1920, 2007.
Yu et al., *Science*, 324 (5928):797-801, 2009.
Zhang et al., *J. Pharmacol. Exp. Ther.*, 311 (1):373-381, 2004.
Zhang, et al., *Circ Res.*, 104 (4):e30-41, 2009.
Zhou et al., *Cell Stem Cell*, 4 (5):381-4, 2009

The invention claimed is:

1. A method for determining the presence of a tissue-specific genetic variation in a test subject, wherein the test subject has a disease of unknown genetic cause that affects a retinal tissue, the method comprising:
    a) creating an induced pluripotent stem (iPS) cell from somatic cells from a sample taken from said test subject;
    b) making a differentiated retinal cell using the iPS cell of step a);
    c) sequencing a first nucleic acid from said differentiated retinal cell; and
    d) comparing said first nucleic acid sequence with a second nucleic acid sequence from a cell from a control individual, thereby determining the presence of tissue-specific genetic variation in the subject.

2. The method of claim 1, wherein said differentiated cell is a neural retina cell.

3. The method of claim 1, wherein said differentiated cell is a retina pigment epithelium (RPE) cell.

4. The method of claim 1, wherein said sequencing comprises DNA sequencing.

5. The method of claim 1, wherein the control individual is one known not to have a selected genetic variation.

6. The method of claim 5, wherein the control cell is from a normal tissue.

7. The method of claim 1, wherein the control cell is prepared by differentiating an iPS cell obtained by reprogramming a normal somatic cell of a control subject.

8. The method of claim 7, wherein the control cell is a retinal cell.

9. The method of claim 1, wherein the control cell is a retinal cell.

10. The method of claim 1, wherein said sequencing comprises RNA sequencing.

\* \* \* \* \*